United States Patent [19]

Muir et al.

[11] Patent Number: 5,364,774
[45] Date of Patent: Nov. 15, 1994

[54] TREPONEMA HYODYSENTERIAE VACCINE

[75] Inventors: Susie Jane Muir; Marcel B. H. Koopman; Johannes G. Kusters, all of Weesp, Netherlands

[73] Assignee: Duphar International Research B.V., Weesp, Netherlands

[21] Appl. No.: 965,668

[22] Filed: Oct. 21, 1992

[30] Foreign Application Priority Data

Oct. 25, 1991 [NL] Netherlands ............... 91202766
Jul. 24, 1992 [NL] Netherlands ............... 92202274

[51] Int. Cl.$^5$ ............... C12P 21/02; C12P 19/34; C12N 15/00; C12N 7/00; C12N 5/00/1/21; C12N 1/16/1/18; C07H 15/12; C07K 3/00
[52] U.S. Cl. ............... 435/69.3; 435/172.3; 435/252.3; 435/240.2; 435/320.1; 435/235.1; 536/23.7; 536/23.2; 530/350; 935/9; 935/29; 935/41; 935/56; 935/63; 935/72; 935/82
[58] Field of Search ............... 435/69.3, 91, 172.3, 435/252.3; 536/27; 530/350; 935/9, 29, 41, 56, 63, 72, 82, 320.1, 235.1, 240.2, 252.3, 255, 256

[56] References Cited

U.S. PATENT DOCUMENTS 5,176,910  1/1993  McCaman et al. ............... 424/92

OTHER PUBLICATIONS

Ter Hunrne et al. FEMS Microbiol. Lett. vol. 92 pp. 109–114 (1992).
Knoop et al Infect. Immun. vol. 31 pp. 193–198 (1981).
Berger et al J. Bacteriol. vol 152 pp. 1241–1247 (1982).
Coreman et al J. Bacteriol. vol. 153 pp. 909–915 (1983).
del Real et al Infect Immun. vol. 57 pp. 2588–2590 (1989).

*Primary Examiner*—Joan Ellis
*Attorney, Agent, or Firm*—Stevens, Davis, Miller & Mosher

[57] ABSTRACT

The present invention is concerned with vaccine for combating Treponema hyodysenteriae infection in swine containing proteins or polypeptides typical of the hemolysin protein of Treponema hyodysenteriae or containing recombinant polynucleotides having as part thereof a polynucleotide coding for said protein or polypeptide, and also is concerned with the preparation of said proteins, polypeptides and polynucleotides.

2 Claims, 9 Drawing Sheets

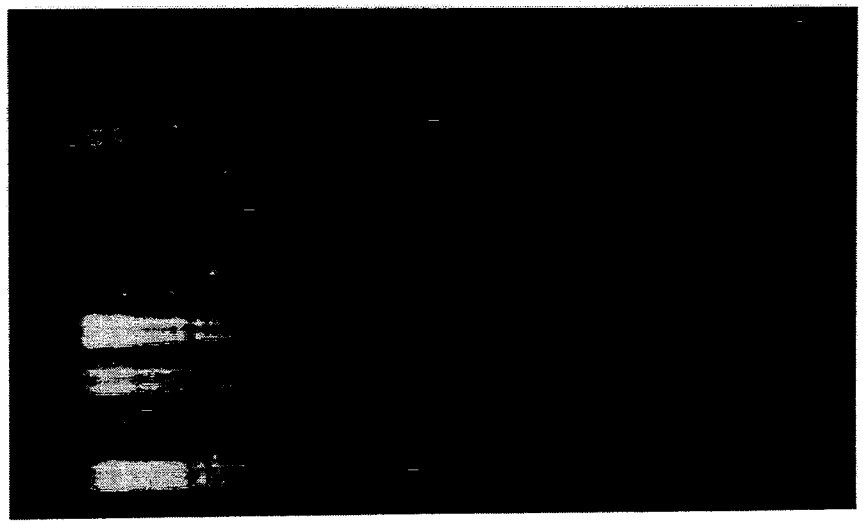

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1498 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: TREPONEMA HYODYSENTERIAE
        ( B ) STRAIN: B 204
        ( H ) CELL LINE: E. COLI JM105 (pJBA) [CBS 512.91]

( i x ) FEATURE:
        ( A ) NAME/KEY: CDS (B) LOCATION: 1..456
(D) OTHER INFORMATION: /product="UNKNOWN PROTEIN"

(ix) FEATURE:
(A) NAME/KEY: intron
(B) LOCATION: 457..470

(ix) FEATURE:
(A) NAME/KEY: CDS
(B) LOCATION: 471..1190
(D) OTHER INFORMATION: /product="HEMOLYSIN PROTEIN"

(ix) FEATURE:
(A) NAME/KEY: intron
(B) LOCATION: 1191..1498

(xi) SEQUENCE DESCRIPTION: SEQ ID NO:1:

| | | | | | | | | | | | | | | | | |
|---|---|---|---|---|---|---|---|---|---|---|---|---|---|---|---|---|
| GAT | CCT | AAT | GCT | GAT | ACT | GAT | GAA | TCT | CCT | GCT | TTA | TTG | ATT | TCT | GCT | 48 |
| Asp | Pro | Asn | Ala | Asp | Thr | Asp | Glu | Ser | Pro | Ala | Leu | Leu | Ile | Ser | Ala | |
| 1 | | | | 5 | | | | | 10 | | | | | 15 | | |
| TCT | ATA | ACT | GAT | ACT | GAT | ACA | GTT | AAA | GTA | ATA | TTA | CAG | GCA | TTT | GCT | 96 |
| Ser | Ile | Thr | Asp | Thr | Asp | Thr | Val | Lys | Val | Ile | Leu | Gln | Ala | Phe | Ala | |
| | | | 20 | | | | | 25 | | | | | 30 | | | |
| GAA | GAT | GTT | ACT | GAT | GAT | ATT | TAT | ACA | ATT | GGC | GGT | AAT | TTA | TGC | TAT | 144 |
| Glu | Asp | Val | Thr | Asp | Asp | Ile | Tyr | Thr | Ile | Gly | Gly | Asn | Leu | Cys | Tyr | |
| | | | 35 | | | | | 40 | | | | | 45 | | | |
| ATA | AAA | GAT | TCT | ATA | TTA | TAT | ATT | TCT | GAT | AAT | TCT | AAT | GTT | ATA | GAT | 192 |
| Ile | Lys | Asp | Ser | Ile | Leu | Tyr | Ile | Ser | Asp | Asn | Ser | Asn | Val | Ile | Asp | |
| 50 | | | | | 55 | | | | | 60 | | | | | | |
| TCT | ATA | ATT | AAT | GGT | GAA | AAG | CCA | GCA | ACA | GCA | TTA | TCT | GCT | GAT | AAA | 240 |
| Ser | Ile | Ile | Asn | Gly | Glu | Lys | Pro | Ala | Thr | Ala | Leu | Ser | Ala | Asp | Lys | |
| 65 | | | | | 70 | | | | | 75 | | | | | 80 | |
| GTT | GAA | ATA | GCT | AAA | AAT | AAT | ACT | ATG | GCT | TTA | TAT | TTA | GAG | TTT | AAT | 288 |
| Val | Glu | Ile | Ala | Lys | Asn | Asn | Thr | Met | Ala | Leu | Tyr | Leu | Glu | Phe | Asn | |
| | | | | 85 | | | | | 90 | | | | | 95 | | |
| TCT | AAT | TTA | TCA | TTA | TAT | GGT | ATT | GGA | GAT | GAA | TAT | ACT | GAA | ACT | TTT | 336 |
| Ser | Asn | Leu | Ser | Leu | Tyr | Gly | Ile | Gly | Asp | Glu | Tyr | Thr | Glu | Thr | Phe | |
| | | | 100 | | | | | 105 | | | | | 110 | | | |
| GAA | TCA | GTT | TAT | ATA | ACT | TCA | AAT | ATA | TTA | GAA | AGC | AAT | CAT | ACT | CAA | 384 |
| Glu | Ser | Val | Tyr | Ile | Thr | Ser | Asn | Ile | Leu | Glu | Ser | Asn | His | Thr | Gln | |
| | | | 115 | | | | | 120 | | | | | 125 | | | |
| ATG | CTT | TTA | AAA | GTA | AAT | ATG | AGA | GAT | AAA | GAA | AGA | AAT | TCT | CTT | TCT | 432 |
| Met | Leu | Leu | Lys | Val | Asn | Met | Arg | Asp | Lys | Glu | Arg | Asn | Ser | Leu | Ser | |
| | | 130 | | | | | 135 | | | | | 140 | | | | |
| ATA | ATA | AAA | TCT | TTC | CTT | GGA | TTA | TAATACTAAT | ATAA | ATG | CGA | TTA | GAT | | | 482 |
| Ile | Ile | Lys | Ser | Phe | Leu | Gly | Leu | | | Met | Arg | Leu | Asp | | | |
| 145 | | | | | 150 | | | | | 1 | | | | | | |
| GAA | TAT | GTG | CAT | AGT | GAA | GGC | TAT | ACA | GAA | AGC | AGA | TCT | AAA | GCA | CAG | 530 |
| Glu | Tyr | Val | His | Ser | Glu | Gly | Tyr | Thr | Glu | Ser | Arg | Ser | Lys | Ala | Gln | |
| 5 | | | | | 10 | | | | | 15 | | | | | 20 | |
| GAT | ATA | ATA | CTA | GCC | GGT | TGT | GTT | TTT | GTT | AAT | GGA | GTA | AAG | GTA | ACT | 578 |
| Asp | Ile | Ile | Leu | Ala | Gly | Cys | Val | Phe | Val | Asn | Gly | Val | Lys | Val | Thr | |
| | | | | 25 | | | | | 30 | | | | | 35 | | |
| TCT | AAG | GCT | CAT | AAA | ATA | AAA | GAT | ACT | GAT | AAT | ATA | GAA | GTT | GTT | CAG | 626 |
| Ser | Lys | Ala | His | Lys | Ile | Lys | Asp | Thr | Asp | Asn | Ile | Glu | Val | Val | Gln | |
| | | | 40 | | | | | 45 | | | | | 50 | | | |
| AAT | ATA | AAA | TAT | GTA | TCA | AGA | GCT | GGA | GAA | AAA | TTA | GAA | AAG | GCG | TTT | 674 |
| Asn | Ile | Lys | Tyr | Val | Ser | Arg | Ala | Gly | Glu | Lys | Leu | Glu | Lys | Ala | Phe | |
| | | 55 | | | | | 60 | | | | | 65 | | | | |
| GTA | GAA | TTT | GGA | ATA | TCT | GTA | GAA | AAT | AAA | ATA | TGT | TTA | GAT | ATA | GGA | 722 |
| Val | Glu | Phe | Gly | Ile | Ser | Val | Glu | Asn | Lys | Ile | Cys | Leu | Asp | Ile | Gly | |
| | | 70 | | | | | 75 | | | | | 80 | | | | |
| GCT | TCT | ACA | GGA | GGA | TTT | ACA | GAT | TGT | CGT | CTT | AAG | CAT | GGT | GCT | AAA | 770 |
| Ala | Ser | Thr | Gly | Gly | Phe | Thr | Asp | Cys | Arg | Leu | Lys | His | Gly | Ala | Lys | |
| 85 | | | | | 90 | | | | | 95 | | | | | 100 | |

| | | | | | | | | | | | | | | | |
|---|---|---|---|---|---|---|---|---|---|---|---|---|---|---|---|
| AAA | GTT | TAT | GCT | CTT | GAT | GTA | GGA | CAT | AAT | CAG | CTA | GTT | TAT | AAA | CTT | 818 |
| Lys | Val | Tyr | Ala | Leu<br>105 | Asp | Val | Gly | His | Asn<br>110 | Gln | Leu | Val | Tyr | Lys<br>115 | Leu |

```
AAA GTT TAT GCT CTT GAT GTA GGA CAT AAT CAG CTA GTT TAT AAA CTT              818
Lys Val Tyr Ala Leu Asp Val Gly His Asn Gln Leu Val Tyr Lys Leu
            105                 110                115

CGT AAT GAT AAT AGG GTA GTG TCA ATA GAA GAT TTC AAT GCC AAA GAT              866
Arg Asn Asp Asn Arg Val Val Ser Ile Glu Asp Phe Asn Ala Lys Asp
            120                 125                130

ATA AAT AAA GAA ATG TTC AAT GAT GAA ATC CCA TCT GTA ATA GTA AGT              914
Ile Asn Lys Glu Met Phe Asn Asp Glu Ile Pro Ser Val Ile Val Ser
            135                 140                145

GAC GTA TCA TTT ATA TCA ATA ACA AAA ATA GCA CCA ATC ATA TTT AAA              962
Asp Val Ser Phe Ile Ser Ile Thr Lys Ile Ala Pro Ile Ile Phe Lys
    150                 155                160

GAA TTA AAT AAT TTA GAG TTT TGG GTA ACT TTA ATA AAA CCA CAA TTT             1010
Glu Leu Asn Asn Leu Glu Phe Trp Val Thr Leu Ile Lys Pro Gln Phe
165                 170                 175                180

GAA GCT GAA AGA GGT GAT GTT TCA AAA GGC GGT ATA ATA CGA GAT GAT             1058
Glu Ala Glu Arg Gly Asp Val Ser Lys Gly Gly Ile Ile Arg Asp Asp
            185                 190                195

ATA CTT AGA GAA AAA ATA TTA AAT AAT GCT ATT TCA AAG ATA ATA GAC             1106
Ile Leu Arg Glu Lys Ile Leu Asn Asn Ala Ile Ser Lys Ile Ile Asp
            200                 205                210

TGC GGA TTT AAA GAA GTT AAT AGA ACC ATC TCT CCT ATA AAA GGT GCT             1154
Cys Gly Phe Lys Glu Val Asn Arg Thr Ile Ser Pro Ile Lys Gly Ala
            215                 220                225

AAA GGT AAT ATA GAA TAT TTA GCT CAT TTT ATT ATT TAATCATTTT                  1200
Lys Gly Asn Ile Glu Tyr Leu Ala His Phe Ile Ile
            230                 235                240

CTATTTTATG TGTATTCTC  TGTTTATATA TTTCATATTC TTTATAGAAG CCTTCTACAT           1260

CATTTACCAT TAAATATCCT TCTTCTGATA TATCTAATGA TTTTATTTTT AATATTTCAT           1320

TTTCTACATT ACTTTATAT  TCTATGCCTA TCATAGAACA AATATCATTT ATATTATATT           1380

GAAATTTTAT TTTGTTTATA TTTTTGAATA AAAGTTCAGT TTTTATTAAC GCTTCTATTA           1440

TTATCACGAA TTTGCTTACT ACTTTATTAG CATTAAAAGA CCTTATTCTA GAAATAGT            1498
```

( 2 ) INFORMATION FOR SEQ ID NO:2:

( i ) SEQUENCE CHARACTERISTICS:
        ( A ) LENGTH: 152 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Asp Pro Asn Ala Asp Thr Asp Glu Ser Pro Ala Leu Leu Ile Ser Ala
 1               5                  10                  15

Ser Ile Thr Asp Thr Asp Thr Val Lys Val Ile Leu Gln Ala Phe Ala
            20                  25                  30

Glu Asp Val Thr Asp Asp Ile Tyr Thr Ile Gly Gly Asn Leu Cys Tyr
            35                  40                  45

Ile Lys Asp Ser Ile Leu Tyr Ile Ser Asp Asn Ser Asn Val Ile Asp
        50                  55                  60

Ser Ile Ile Asn Gly Glu Lys Pro Ala Thr Ala Leu Ser Ala Asp Lys
65                  70                  75                  80

Val Glu Ile Ala Lys Asn Asn Thr Met Ala Leu Tyr Leu Glu Phe Asn
                85                  90                  95

Ser Asn Leu Ser Leu Tyr Gly Ile Gly Asp Glu Tyr Thr Glu Thr Phe
                100                 105                 110

Glu Ser Val Tyr Ile Thr Ser Asn Ile Leu Glu Ser Asn His Thr Gln
            115                 120                 125
```

|     |     |     |     |     |     |     |     |     |     |     |     |     |     |     |
| --- | --- | --- | --- | --- | --- | --- | --- | --- | --- | --- | --- | --- | --- | --- |
| Met | Leu | Leu | Lys | Val | Asn | Met | Arg | Asp | Lys | Glu | Arg | Asn | Ser | Leu | Ser |
|     | 130 |     |     |     |     | 135 |     |     |     | 140 |     |     |     |     |     |
| Ile | Ile | Lys | Ser | Phe | Leu | Gly | Leu |
| 145 |     |     |     |     | 150 |     |     |

( 2 ) INFORMATION FOR SEQ ID NO:3:

( i ) SEQUENCE CHARACTERISTICS:
        ( A ) LENGTH: 240 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Met | Arg | Leu | Asp | Glu | Tyr | Val | His | Ser | Glu | Gly | Tyr | Thr | Glu | Ser | Arg |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ser | Lys | Ala | Gln | Asp | Ile | Ile | Leu | Ala | Gly | Cys | Val | Phe | Val | Asn | Gly |
|     |     |     | 20  |     |     |     |     | 25  |     |     |     | 30  |     |     |     |
| Val | Lys | Val | Thr | Ser | Lys | Ala | His | Lys | Ile | Lys | Asp | Thr | Asp | Asn | Ile |
|     |     | 35  |     |     |     |     | 40  |     |     |     | 45  |     |     |     |     |
| Glu | Val | Val | Gln | Asn | Ile | Lys | Tyr | Val | Ser | Arg | Ala | Gly | Glu | Lys | Leu |
|     | 50  |     |     |     |     | 55  |     |     |     |     | 60  |     |     |     |     |
| Glu | Lys | Ala | Phe | Val | Glu | Phe | Gly | Ile | Ser | Val | Glu | Asn | Lys | Ile | Cys |
| 65  |     |     |     |     | 70  |     |     |     |     | 75  |     |     |     |     | 80  |
| Leu | Asp | Ile | Gly | Ala | Ser | Thr | Gly | Gly | Phe | Thr | Asp | Cys | Arg | Leu | Lys |
|     |     |     |     | 85  |     |     |     |     | 90  |     |     |     |     | 95  |     |
| His | Gly | Ala | Lys | Lys | Val | Tyr | Ala | Leu | Asp | Val | Gly | His | Asn | Gln | Leu |
|     |     |     | 100 |     |     |     |     | 105 |     |     |     |     | 110 |     |     |
| Val | Tyr | Lys | Leu | Arg | Asn | Asp | Asn | Arg | Val | Val | Ser | Ile | Glu | Asp | Phe |
|     |     | 115 |     |     |     |     | 120 |     |     |     |     | 125 |     |     |     |
| Asn | Ala | Lys | Asp | Ile | Asn | Lys | Glu | Met | Phe | Asn | Asp | Glu | Ile | Pro | Ser |
|     | 130 |     |     |     |     | 135 |     |     |     |     | 140 |     |     |     |     |
| Val | Ile | Val | Ser | Asp | Val | Ser | Phe | Ile | Ser | Ile | Thr | Lys | Ile | Ala | Pro |
| 145 |     |     |     |     | 150 |     |     |     |     | 155 |     |     |     |     | 160 |
| Ile | Ile | Phe | Lys | Glu | Leu | Asn | Asn | Leu | Glu | Phe | Trp | Val | Thr | Leu | Ile |
|     |     |     |     | 165 |     |     |     |     | 170 |     |     |     |     | 175 |     |
| Lys | Pro | Gln | Phe | Glu | Ala | Glu | Arg | Gly | Asp | Val | Ser | Lys | Gly | Gly | Ile |
|     |     |     | 180 |     |     |     |     | 185 |     |     |     |     | 190 |     |     |
| Ile | Arg | Asp | Asp | Ile | Leu | Arg | Glu | Lys | Ile | Leu | Asn | Asn | Ala | Ile | Ser |
|     |     | 195 |     |     |     |     | 200 |     |     |     |     | 205 |     |     |     |
| Lys | Ile | Ile | Asp | Cys | Gly | Phe | Lys | Glu | Val | Asn | Arg | Thr | Ile | Ser | Pro |
|     | 210 |     |     |     |     | 215 |     |     |     |     | 220 |     |     |     |     |
| Ile | Lys | Gly | Ala | Lys | Gly | Asn | Ile | Glu | Tyr | Leu | Ala | His | Phe | Ile | Ile |
| 225 |     |     |     |     | 230 |     |     |     |     | 235 |     |     |     |     | 240 |

TREPONEMA HYODYSENTERIAE VACCINE

The present invention is concerned with a vaccine for combating Treponema hyodysenteriae infection and with recombinant polynucleotides and polypeptides for the preparation of such a vaccine.

*Treponema hyodysenteriae*, the etiological agent of swine dysentery is an anaerobic, beta-hemolytic spirochete found in the porcine large intestine. Upon infection this pathogen secretes a hemolysin which is thought to play an essential role in the pathogenesis of the disease. The disease is characterized by a mucohemorrhagic diarrhoea. This seems to be associated with the extensive superficial necrosis of the luminal epithelial lining and of the crypts of Lieberkuhn.

It has been found that in vivo, during the actual disease course, the hemolysin does not induce an immunogenic response which could be serologically demonstrated up till now.

However, according to the present invention a vaccine containing hemolysin or an immunogenic fragment thereof can be used in combatting swine dysentery.

Accordingly, the present invention is concerned with a substantially pure preparation of Treponema hyodysenteriae hemolysin protein or polypeptide hemolysin protein fragments (hemolysin polypeptides) having at least part of the amino acid sequence of SEQUENCE ID NO: 1.

More in particular, the hemolysin protein and polypeptides derived thereof are able to elicit an immune response against *Treponema hyodysenteriae*.

Furthermore, the present invention is not only concerned with the hemolysin protein and polypeptides but also with DNA of SEQUENCE ID NO: 1 and fragments thereof, and with polynucleotides which hybridize to said DNA and fragments thereof and which code for a polypeptide having the properties of the hemolysin protein of *Treponema hyodysenteriae*.

The present invention is concerned also with a polynucleotide which codes for a polypeptide having the immunogenic properties of the hemolysin protein of *Treponema hyodysenteriae* wherein at least part of the codons of the DNA of SEQUENCE ID NO: 1 or of the fragments thereof, or of the abovementioned hybridizing polynucleotide is replaced by alternative codons for the same amino acid.

One of the properties of the hemolysin protein resides in eliciting an immune response.

Small antigens often are useless as immunogens. Therefore the hemolysin protein or polypeptides may be prepared as homopolymers (a multitude of indentical hemolysin polypeptides coupled) or heteropolymers (one or more hemolysin polypeptide coupled to one or more different hemolysin polypeptides, or coupled to one or more different polypeptides characteristic of *Treponema hyodysenteriae* or an other pathogen), or may be coupled to one or more other compounds in order to enhance immunogenicity.

According to the present invention the hemolysin polypeptide, in any of the modifications mentioned above, may be prepared by recombinant DNA techniques or may be prepared synthetically, e.g. by homogeneous or by solid state polypeptide synthesis.

The particular amino acid sequences of suitable hemolysin potypeptides may be derived from the amino acid sequence according to SEQUENCE ID NO: 1 and optionally also from the spatial configuration of the hemolysin protein.

A number of methods has been developed to predict the location of immunogenically important epitopes on proteins. The outcome of the combined predictions gives a good forecast of antigenic sites.

Suitable hemolysin polypeptides may be selected from the most hydrophilic parts of the hemolysin protein, e.g. by applying the technique described by Hopp and Woods (T. P. Hopp and K. R. Woods K. R. (1981): Proc. Natl. Acad. Sci, USA. 78, 3824–3828). Another suitable method for selecting such polypeptides is described by Chou and Fasman (P. Y. Chou and G. D. Fasnnan (1987)Advances in Enzymology 47, 45–148).

BRIEF DESCRIPTION OF THE DRAWINGS

FIG. 1 represents a hydrophylicity profile of the protein sequence of *Treponema hyodysenteriae* hemolysin, computed using an average group length of 6 amino acids. This results in a prediction of antigenic determinants according to Hopp and Woods, 1981.

FIG. 2 represents the predicted flexibility of *Treponema hyodysenteriae* hemolysin from amino acid 1 to amino acid 240. The y axis value represents the B[norm]. (Karplus, P. A. and G. E. Schultz, 1985. Naturwissenschaften 72, 212–213).

FIG. 3 represents a beta-turn probability profile of *Treponema hyodysenteriae* hemolysin from amino acid 1 to amino acid 240, according to Chou, P. Y. and G. D. Fasman, 1979 (Biophys. J. 26,367–384). The y axis values represent the probability p(turn)*$10^4$.

FIG. 4 represents a plot of the probablity profiles in the 3 conformations for the sequence of *Treponema hyodysenteriae* hemolysin, according to O. Gascuel and J. L. Golmard, 1988 (CABIOS 4,357–365). The extent of the regions predicted in each of the conformations are indicated on top of the graphs.

FIG. 5 presents a prediction of the secondary structure of the sequence of Treponema hyodysenteriae hemolysin according to J. Novotny and C. Auffray, 1984 (Nucleic Acids Research 12, 243–255).

FIGS. 7A and 7B establish the conservation of the hemolysin gene within Treponemal species.

Figure 1:
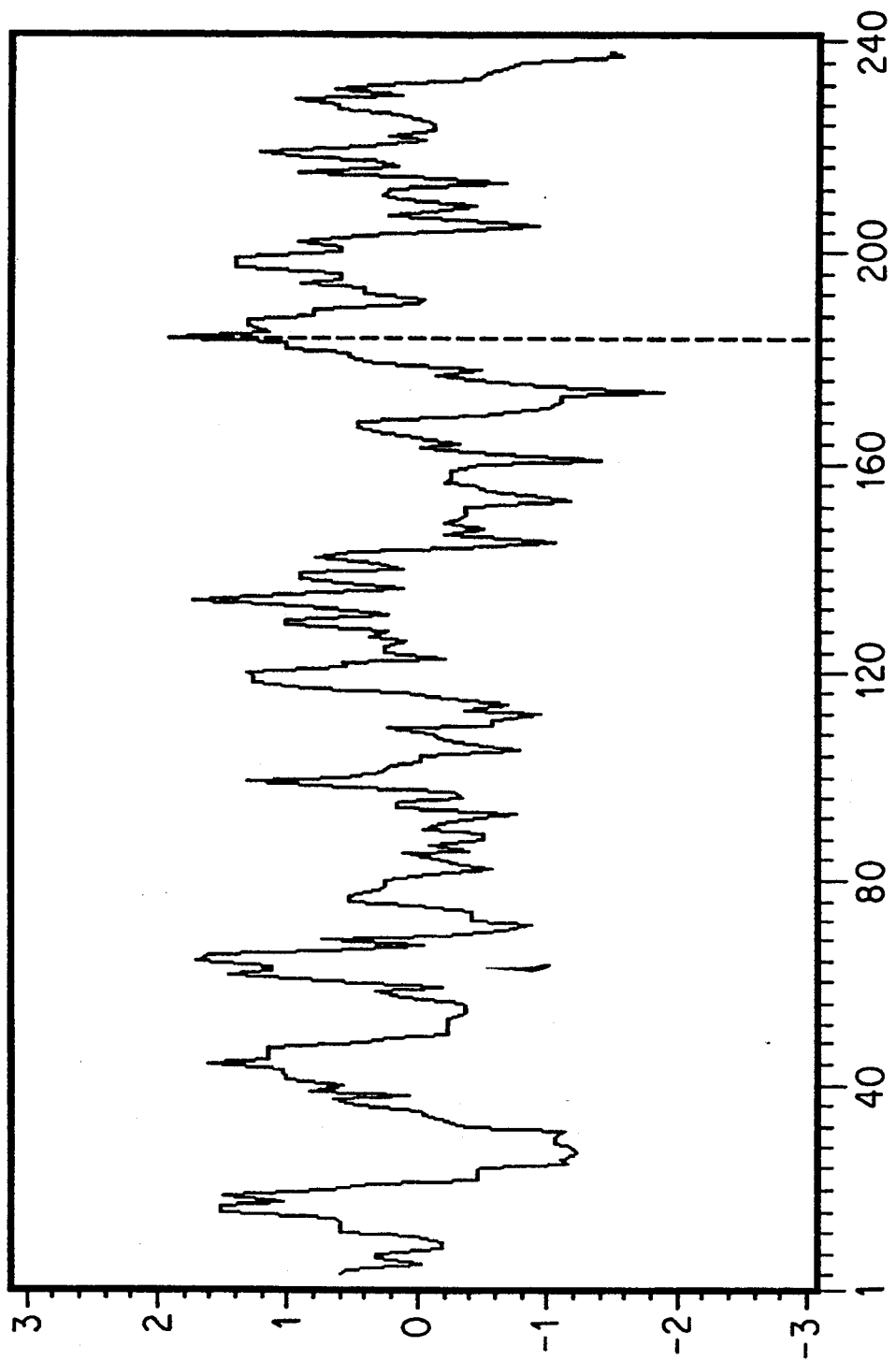
FIGS. 1–5 show the various algorithms that have been used to finally predict the antigenically important regions at the *Treponema hyodysenteriae*-hemolysin-protein.
Figure 2:
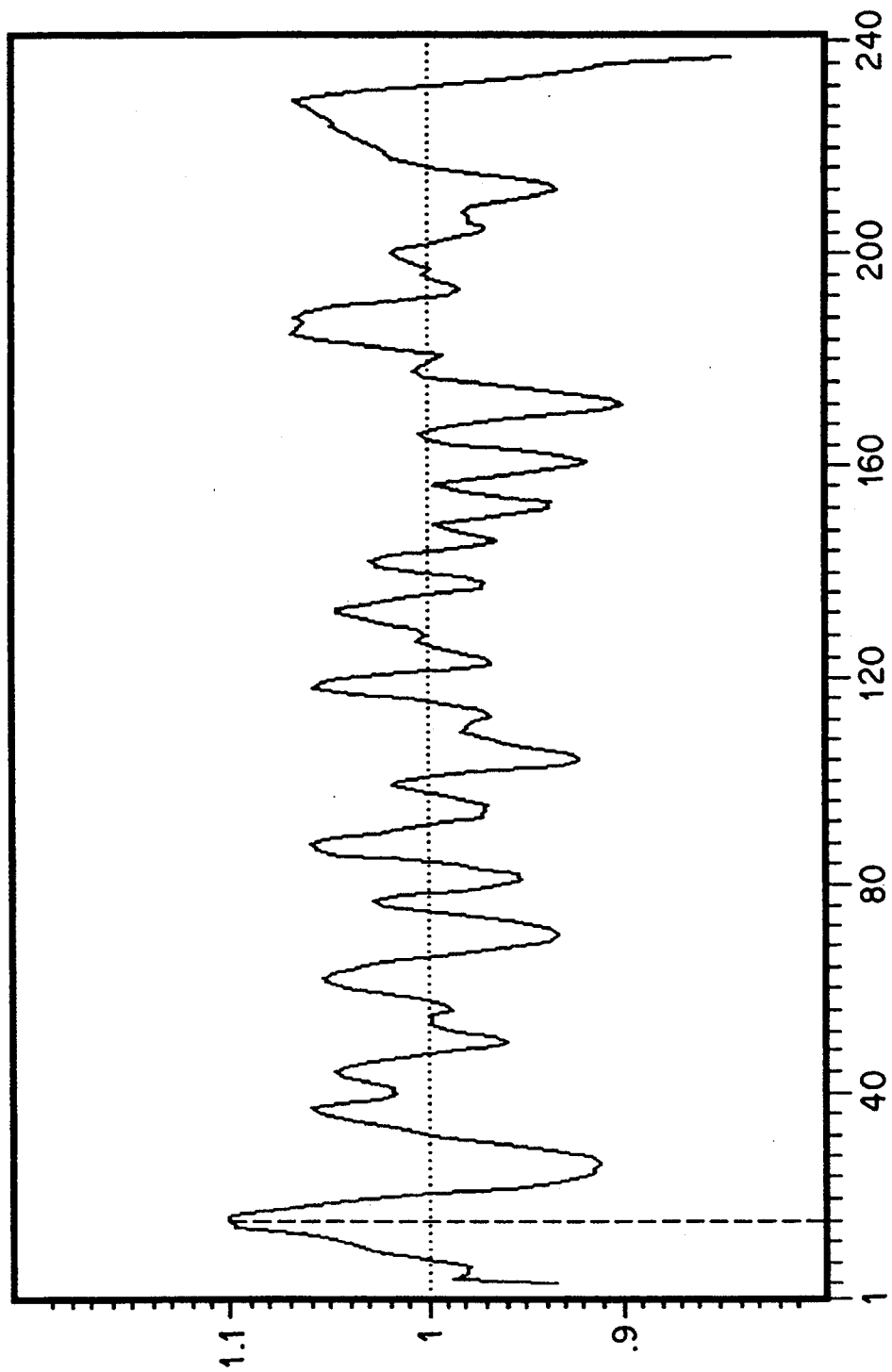
Figure 3:
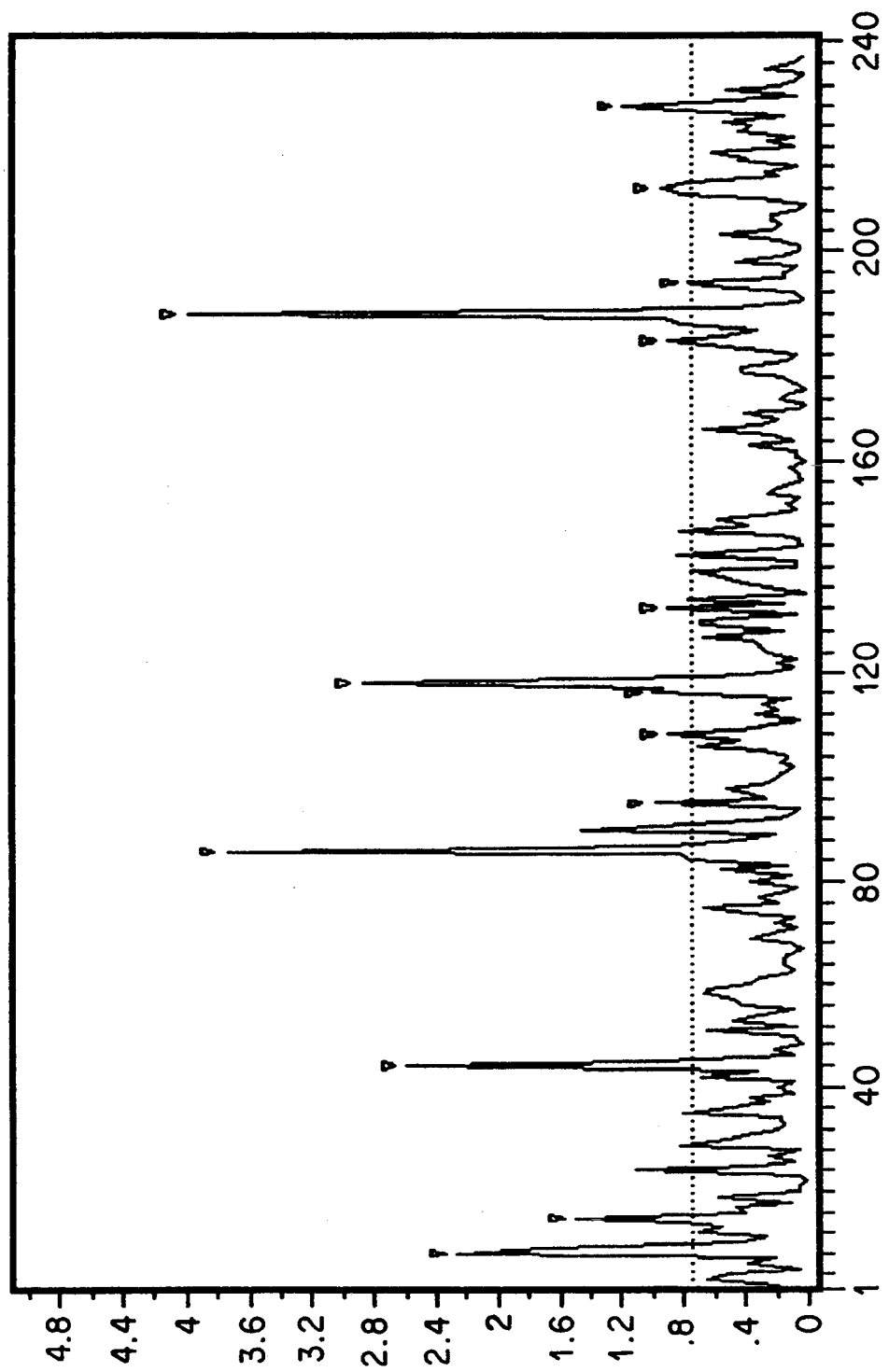
Figure 4:
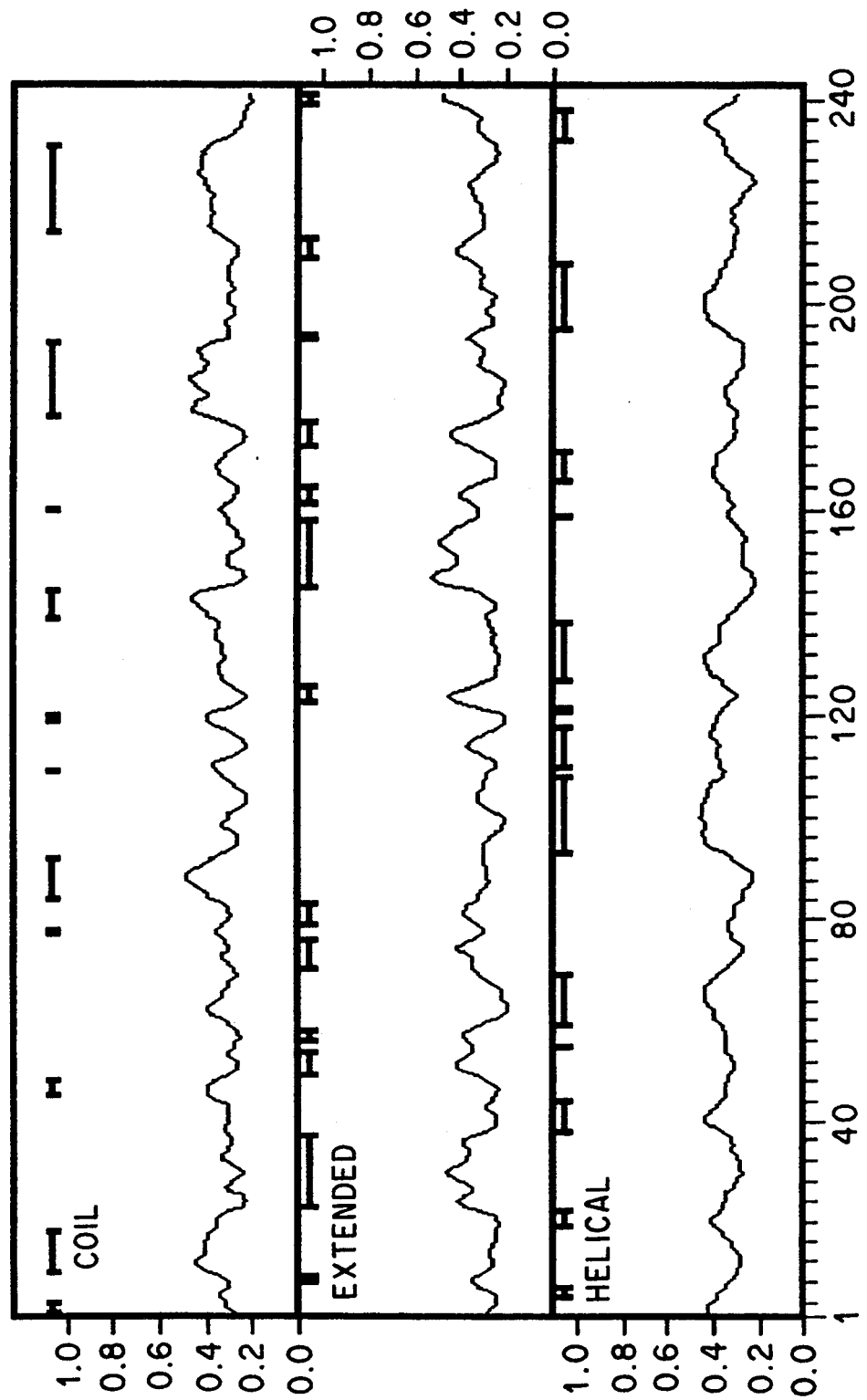
Figure 5:
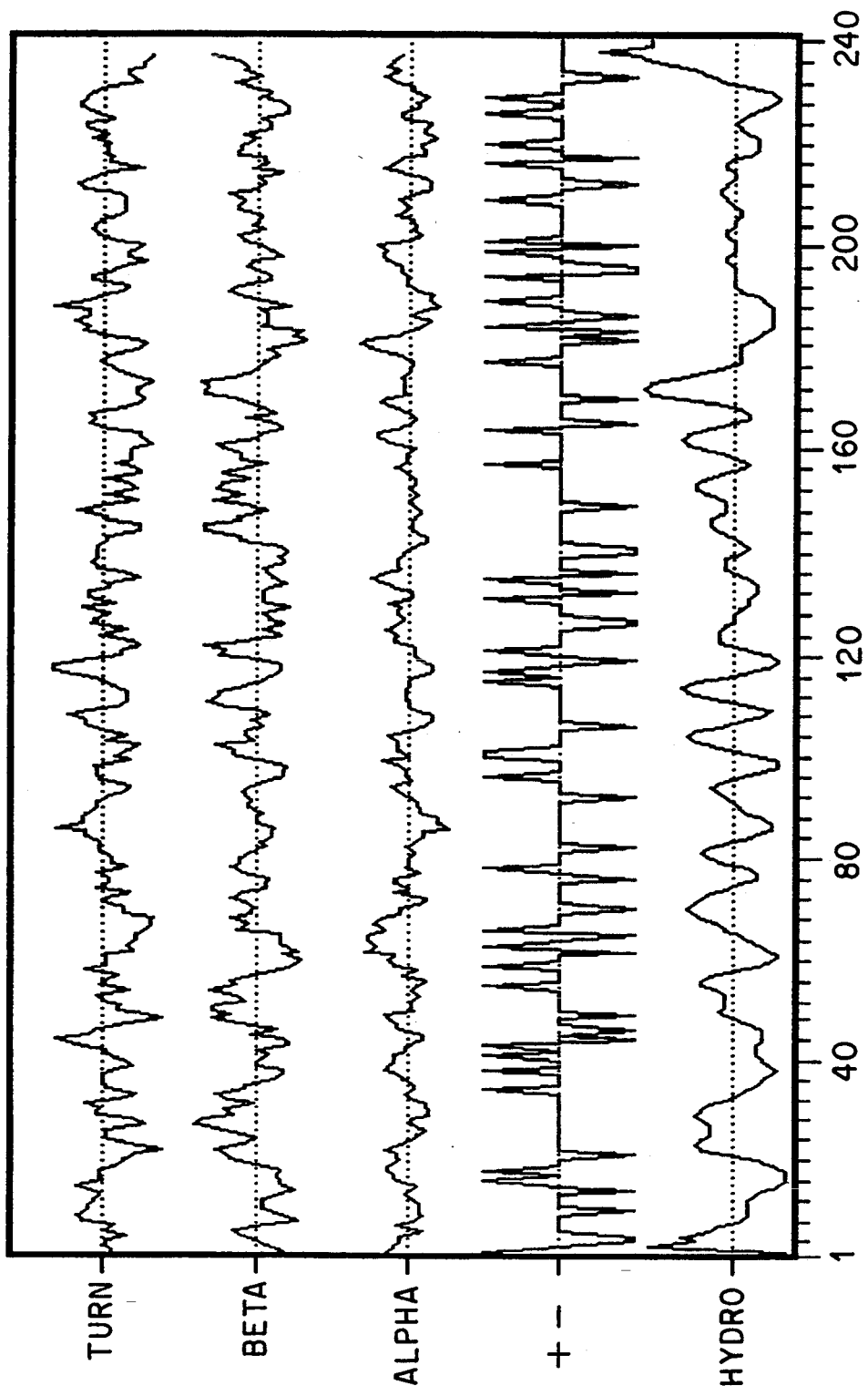

Additional information on the location of relevant epitopes can be obtained using the PEPSCAN-method, developed by Geysen and Meloen (H. M. Geysen, R. H.

Meloen, and S. J. Barteling (1984): Proc. Natl. Acad. Sci., 81 (13); 3998–4002).

This method uses synthetic peptides of sufficient length to react in an enzyme-linked immunosorbent assay. These peptides are synthesised according to a given DNA-sequence. They are characterised by the fact that the first peptide covers amino acid nr. 1–9, the second peptide covers amino acid nr. 2–10 etc.

Each peptide is tested for its reactivity with antisera or monoclonal antibodies. Reactive peptides must then represent an immunogenic epitope.

Furthermore, to identify immunoreactive epitopes (and to correlate these reactivities with the physical map of the hemolysin) DNA fragments from the hemolysin gene can be expressed in the pEX plasmids (K. Stanley and J. P. Luzio, 1984. EMBO J. 3, 1429–1434, and J. G. Kusters, E. J. Jager and E. A. M. Van der Zeijst, 1989. Nucl. Acids Res., 17, 8007). In this system, heterologous expression leads to the synthesis of a C-terminal extension of the cro-β-galactosidase hybrid protein. Restriction-endonuclease sites in the hemolysin DNA sequences can be used to obtain fragments of the hemolysin gene for insertion into the pEX plasmids. pEX clones synthesizing fusion proteins derived from different overlapping regions of the hemolysin are then used for further characterization. The pEX encoded hemolysin fragments are purified, fractionated by polyacrylamide gel electrophoresis, and blotted to nitrocellulose membranes. These membranes are then reacted with sera from immune pigs. Only the fragments containing the immuno reactive epitopes react with these sera. To delineate the minimal length of the epitopes, the DNA inserts of the reactive clones can be progressively shortened by Exonuclease III digestion, or by cloning synthetic oligonucleotides encoding small overlaping parts of the hemolysin (J. G. Kusters, E. J. Jager, G. Koch, J. A. Lenstra, G. Koch, W. P. A. Posthumus, R. H. Meloen and B. A. M. Van der Zeijst, 1989. J. immunol., 143, 2692–2698). The epitopes can then be tested for their protective effects.

According to a particular embodiment of the present invention an hemolysin-protein-specific polypeptide is produced by expression of a polynucleotide having at least part of the poiynucleotide SEQUENCE ID NO: 1 forming part of a recombinant polynucleotide. The recombinant polynucleotide preferably may be based on a vector with a *Treponema hyodysenteriae*-specific polynucleotide fragment inserted therein. Suitable vectors are plasmids, bacteriophages, cosmids, viruses, minichromosomes or stably integrating vectors; the latter in particular for plant or animal cells. Generally these vectors have the property of autonomous replication except for the stably integrating vectors which insert themselves in the genetic material of the host cell and replicate with the host's genetic material. Suitable host cells may be either prokaryotic or eukaryotic, such as bacteria, yeasts, mycoplasms, algae, plant cells or animal cells; the plant cells or animal cells may be cultivated in vitro or may form part of an intact plant or animal, respectively. The recombinant polynucleotide may contain as an insert a complete polynucleotide coding for hemolysin protein or a fragment thereof. The insert may comprise a single coding sequence, or multiple copies of the same coding sequence, or a hybrid polynucleotide containing at least one hemolysin protein coding sequence and at least one second sequence such as a different part of the hemolysin protein coding sequence or a polynucleotide coding for a protein characteristic of an other pathogen or for an inert protein functioning as a carrier for a small hemolysin-polypeptide.

A specific case of the above embodiment is concerned with recombinant polynucleotides with viral vectors, directly useful as so-called vector vaccines. The viruses applicable for this purpose should have the ability to replicate in the animals to be immunized, i.e. in swines. These viruses, furthermore, should possess a genomic region suitable for insertion of a foreign gene (e.g. coding for the *Treponema hyodysenteriae*-hemolysin protein or polypeptide) which is also to be expressed in the vaccinated animal. Suitable viruses for this purpose are for example enteral viruses such as certain adeno viruses.

As was indicated above, the proteins and polypeptides, and the recombinant polynucleotides according to the invention are useful in the preparation of vaccines. Hence, these vaccines also form part of the invention.

A particular application of the present invention is concerned with bacterial vector vaccines. Herein bacteria capable of colonizing swines are transformed in order to enable them to express a hemolysin protein or hemolysin polypeptide in such a way that it will lead to an immunogenic respons against *Treponema hyodysenteriae*. Suitable bacteria for this purpose are e.g. Salmonella bacteria.

A vaccine according to the invention may also contain auxiliary vaccine constituents, such as carriers buffers, stabilizers, solubilizers, adjuvants and preservatives. Advantageously these vaccines are freeze-dried products which are reconstituted by the addition of a suitable liquid (water, buffer) prior to application.

The vaccine can be applied e.g. orally, intranasally or intramusculariy.

The vaccine may additionally contain other immunogens for swines, such as immunogenic material characteristic of viruses such as pseudorabies virus, influenza virus, transmissible gastroenteritis virus, parvo virus, porcine endemic diarhoea virus, hog cholera virus, or immunogenic material characteristic of mycoplasms, such as *Mycoplasma hyopneumoniae* and mycoplasma lyorhinis, or immunogenic material characteristic of bacteria, such as *Escherichia coil, Bordetella bronchiseptica*, Leptospira, *Actinobaccilus pleuropneumoniae, Pasteurella multosida, Streptococcus suis*.

The invention is illustrated by the following working Examples.

EXAMPLE 1

Cloning and Localization of the Hemolysin Gene

Materials and Methods

Bacterial strains and culture conditions.

T. hyodysenteriae strains are classified according to their serotypes which are probably LPS determined. The origin and serotypes of the treponemes used in this study have been described by M. E. Mapother (M. E. Mapother and L. A. Joens. 1985. New serotypes of Treponema hyodysenteriae. J. Clin. Microbiol. 22:161–164), who kindly supplied T. hyodysenteriae strains B234, B204, B169, A-1, B8044, B6933, and Ack 300/8 (serotypes 1, 2, 3, 4, 5, 6, and 7, respectively), T. hyodysenteriae strain B204 (serotype 2) attenuated through 124 consecutive passages, and T. innocens strain B256. All treponemes were grown in trypticase soy medium (Difco Laboratories, Detroit, Mich., USA) supplemented with 5% FBS (Flow) as described by Halter and Joens (1988; Infec. Immun. 56, 3152–3156), bacterial cell pellets were washed in TE and frozen at −70° C. The plasmid pUC 19 and the phagemids pBluescript pKS+ and pSK+ (Stratagene Cloning Systems, La Jolla, Calif., USA) were utilized for the cloning procedures. Escherichia coil (E. coil) K12 strain DH5-α(Gibco BRL, Gaithersburg, Md., USA) was used as a host for these vectors.

Preparation of T. hyodysenteriae chromosomai DNA

Molecular-grade chemicals and enzymes were from Sigma Chemical Co. (St. Louis, Mo. USA). Frozen bacterial cell pellets from 1 liter cultures were thawed in 25 ml buffer containing 100 mmol/l Tris-HCl pH 8.0, 100 mmol/l EDTA, 150 mmol/l NaCl, and 10 mg/ml lysozyme. Following a 1 hour incubation at 37° C. 0.5 ml of RNAseA was added to the cells which were then incubated an additional 15 minutes at 70° C. Cell lysis was completed by the addition of 2.5 ml of 30% Sarkosyl, gentle mixing, and incubating at 70° C. for 20 minutes followed by a 1 hour incubation at 37° C. Predigested pronase, (final concentration of 10 mg/ml) was added and incubation continued for 4 hours at 37° C. The lysate was transferred to dialysis tubing and dialyzed overnight in 6 liters of TE (10 mmol/l Tris-HCl), 1 mmol/l EDTA, pH 8.0. The DNA was then once gently extracted with TE saturated phenol, extracted with chloroform:isoamyl alcohol (24:1), dialyzed for 6 hours in TE, and ethanol precipitated. Chromosomal DNA was resuspended in TE at a concentration of 1 mg/ml. DNA prepared in this manner was used for library construction and Southern blot analysis.

Construction of T. hyodysenteriae genomic library

Restriction enzymes, calf intestinal phosphatase, T4 DNA ligase, bovine pancreas RNAase A, and the Klenow fragment of E. coil DNA polymerase 1 were obtained from Boehringer Mannhelm Biochemicals (Indianapolis, Ind., USA). All enzymes were used under the conditions specified by the manufacturer. Standard cloning protocols (T. Maniatis, E. F. Fritsch, and J. Sambrook. 1982. Molecular Cloning: a laboratory manual. Cold Spring Harbor Laboratory, Cold Spring Harbor, N.Y., USA) were followed for all DNA manipulations. T. hyodysenteriae DNA was digested with the restriction enzyme MboI and ligated with T4 DNA ligase to BamHI restricted, dephosphorylated pUC19. E. coli DH5α cells were transformed with the ligation mix and recombinants screened for hemolysin production.

Screening for hemolytic clones

Figure 6:
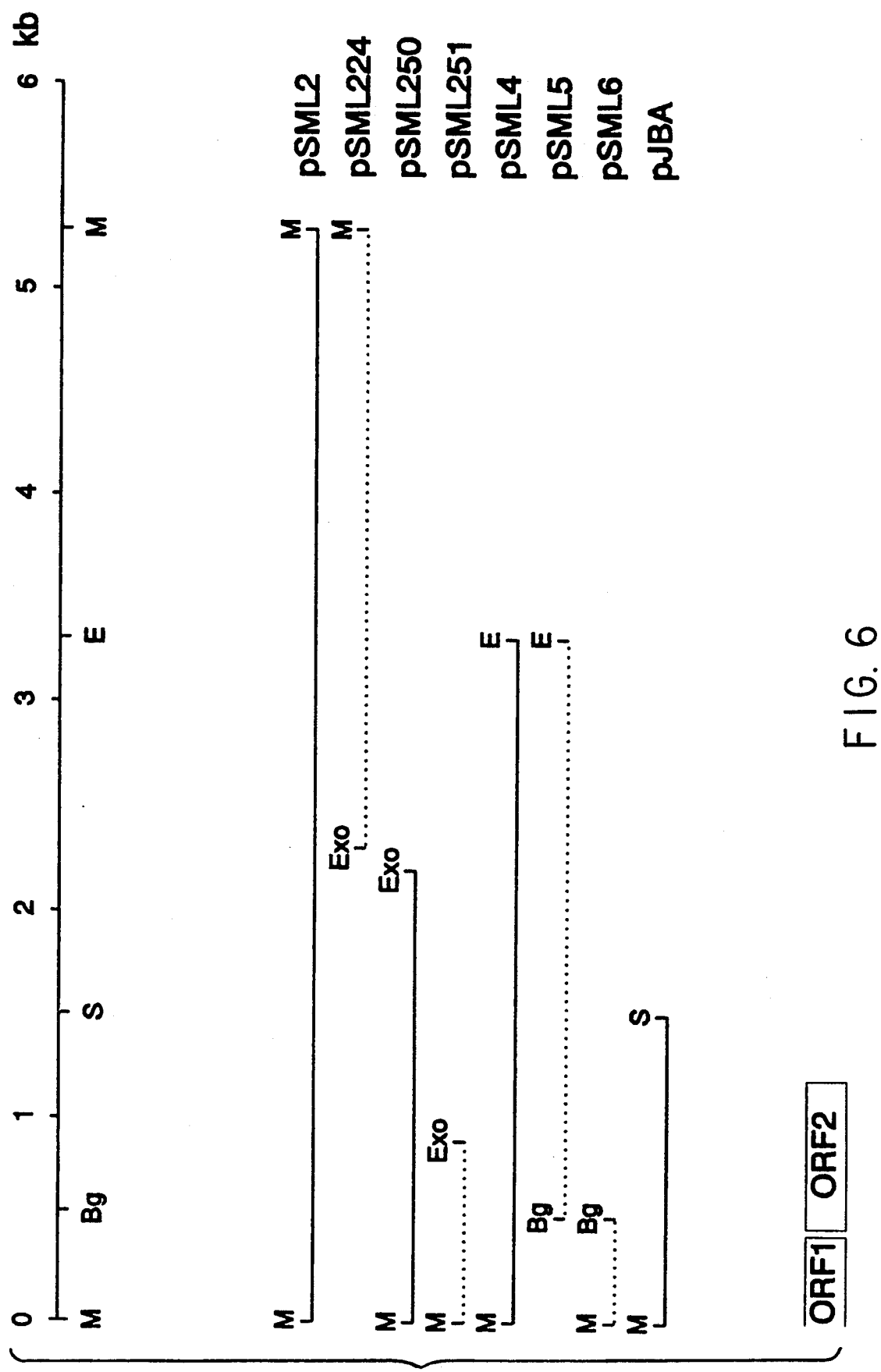
FIG. 6 shows Exonuclease III constructed subclones of pSML2.

Recombinants were plated on trypicase soy agar containing 4% defibrinated SRBC (Colorado Serum Co., Denver, Colo., USA) and 100 ug/ml carbenicilin (TSA blood plates). Plates were incubated at 37 ° C. for 24–36 hours to detect hemolytic colonies. A single hemolytic clone, designated pSML2, was chosen for further analysis. From this clone all subclones were constructed (FIG. 6).

Southern blotting

Chromosomal DNA was digested with the restriction enzyme EcoRV, electrophoresed in a 0.8% agarose gel, and transferred to nylon membrane. A 1.5 bp ScaI/BamHI fragment from pJBA, the smallest subclone of pSML2 containing the active hemolysin gene, was random primer labeled with $^{32}p$ (A. P. Feinborg, and B. Vogelstein. 1983. A technique for radiolabelling DNA restriction endonuclease fragments to high specificity. Anal. Blochem. 132:6–13.). Prehybridization, hybridization and washing of the membrane were at 60° C. essentially as described (Maniatis et al., supra). The membrane was exposed to Kodak X-OMAT AR film at −70° C. for periods of 2 to 18 hours.

Osmotic Release of the Recombinant Hemolysin

To characterize the recombinant hemolysin, E. coil DH5α(pJBA) cells were subjected to osmotic shock essentially as described by Heppel (L. A. Heppel 1967. Selective release of enzymes from bacteriae. Science 156:1451–1455).

Hemolysin Assays

Aliquots of the osmotic shock supernatants were adjusted to a final concentration of 140 mmol/l NaCl and added to sheep red blood cells (SRBC) which were washed and resuspended at 10% in 140 mmol/l NaCl. The mixtures were incubated at 37 ° C. for one hour and the release of hemoglobin from the red cells determined by reading the optical density of the supernatant at 540 nm.

Extraction of hemolysin from the native organism

Hemolysin was extracted from strain B204 using an RNA core extraction procedure (K. A. Kent, R. M. Lemeke, and R. J. Lysons. 1988. Production, purification and molecular weight determination of the haemolysin of Treponema hyodysenteriae. J. Mod. Microbiol. 27:21 5–224) and concentrated.

Cytotoxity Assays

Osmotic shock supernatant from E. coil DHS5α(pJBA), DH5α(pSML5) and DH5α(pUC-19), and RNA core-hemolysin were filtered sterilized and added to $5 \times 10^4$ Chinese Hamster Ovary (CHO) cells/well as two-fold dilutions from 1:2 to 1:160. Cells were incubated at 37° C. for 24 hours in a $CO_2$ incubator and examined at various time intervals for cytopathic effect (CPE). CPE was determined by direct visual inspection of the CHO monolayer at 1, 12, and 24 hours following the addition of hemolysin to each well.

DNA Sequencing

The 1.5 kbp ScaI/BamHI insert in pJBA was subcloned into M13mp18 and M13mp19. Both strands were sequenced by dideoxynucleotide chain termination using a Sequenase kit (United State Biochemical, Cleveland, Ohio). The −40M13 sequencing primer was used to ascertain the sites of insertion and the first one hundred bases at the 3' and 5' regions of the gene. Subsequently, based on previous sequence, oligonucleotide primers synthesized on a Cyclone Plus DNA synthesizer (Millipore Corp., Bedford, Mass., USA) were used to sequence the total hemolysin gene.

RESULTS

Cloning and localization of the hemolysin gene

The plasmid vector pUC19 was utilized to prepare a library of *T. hyodysenteriae* strain B 204. Plasmid DNA from the hemolytic clone, pSML2, contained a 5 kb fragment of *T. hyodysenteriae*. Using the enzymes exonuclease III and mung bean nuclease any deletion from the left hand end of pSML2 resulted in the immediate abrogation of hemolytic activity (pSML244). It was possible to remove 3.1 kb of DNA from the right hand end of pSML2 and retain full hemolytic activity in the resultant 2.2 kb plasmid, pSML250. Deletions greater than 3 kb abolished all hemolytic activity. These results are summarized in Table 1.

TABLE 1

| Plasmid | Active | Vector | Insert Size KB |
| --- | --- | --- | --- |
| pSML2 | + | pUC19 | 5.3 |
| pSML244 | − | pUC19 | 3.0 |
| pSML250 | + | pUC19 | 2.2 |
| pSML251 | − | pUC19 | 0.9 |
| pSML4 | + | pUC19 | 3.3 |
| pSML5 | − | pUC19 | 2.8 |
| pJBA | + | pKS+ | 1.5 |
| pSML6 | − | pKS+ | 0.5 |

Exonuclease III results (FIG. 6) were confirmed by subcloning restriction enzyme fragments of pSML2 in the pBluescript vectors. The EcoR1 (E) subclone, pSML4, contained a 3.3 kb fragment and was as hemolytic as the parent plasmid. As an additional manipulation to narrow down the DNA region encoding hemolytic activity, pSML4 was BglII/HincII digested, BglII(B) ends were blunted using Klenow, and plasmid DNA was ligated and transformed into competent *E. coli* DH5α. The resultant 2.75 kb plasmid, pSML5, was not hemolytic. Digestion of pSML4 with ScaI/-BamHI(S:ScaI) produced a 1.5 kb fragment which, when subcloned into EcoRV/BamHI restricted pBluescript phagemid pKS+ or pSK+, yielded the plasmid, pJBA, which was as hemolytic as either pSML2 or pSML4. This plasmid pJBA in *E. coli* JM105 was deposited with the Centraalbureau voor Schimmelcultures at Baarn, The Netherlands under deposit number No 512.91. Thus, the loss of 500 base pairs (pSML6) from the right hand end of pSML4 abbrogated all hemolytic activity, whereas no effect on hemolytic activity was noted with the loss of 1.8 kb from its left hand end (FIG. 6).

Conservation of the hemolysin gene within treponemal species. To determine whether or not the hemolysin gene (or a homologous gene) was present in *T. innocens* and conserved in all hemolytic pathogenic serotypes of *T. hyodysenteriae*, Southern hybridization of treponemal chromosomal DNA with the hemolysin gene was performed. EcoRV was used to digest chromosomal DNA. In all serotypes of *T. hyodysenteriae* a single 4.8 kb EcoRV fragment strongly hybridized with the 1.5 kb ScaI/BamHI fragment pJBA containing the hemolysin gene whereas no hybridization occurred with the non-pathogenic treponome, T. innocens (FIG. 7).

In this experiment the Treponema species listed in Table 2 were tested.

TABLE 2

| Lane | Treponema species |
| --- | --- |
| 1 | *T. hyodysenteriae* strain B204, serotype 2 |
| 2 | *T. innocens* strain, B256 |
| 3 | *T. hyodysenteriae* strain A-1, serotype 4 |
| 4 | *T. hyodysenteriae* strain B204 attenuated at 124 passages |
| 5 | *T. hyodysenteriae* strain 6933, serotype 6 |
| 6 | *T. hyodysenteriae* strain, Ack300/8 serotype 7 |
| 7 | *T. hyodysenteriae* strain B169, serotype 3 |
| 8 | *T. hyodysenteriae* strain B234, serotype 1 |
| 9 | *T. hyodysenteriae* strain 8044, serotype 5 |

One fragment at 4.8 kb hybridized in all pathogenic biotypes whereas no hybridization was detected with T. innocens even upon prolonged (>48 hours) exposure.

Further, the hemolysin gene shared no homology with the isolated, unrestricted plasmid present in *T. hyodysenteriae*. No hemology with chromosomal DNA from other enteric pathogens (*Salmonella typhimurium* and hemolytic enteropathogenic *E. coli*) was demonstrated.

Sequence of hemolysin

The hemolysin gene was exceptionally adenosine-plus-thymidine rich (75%) as has been reported for pathogenic and non-pathogenic strains of Treponemes (R. M. Miao, A. H. Fieldsteel, and D. L. Harris. 1970. Genetics of Treponema: characterization of *Treponema hyodysenteriae* and its relationship to *Treponema pallidum*. Infect. Immun. 22:736–739.). The sequence is shown in SEQUENCE ID NO. 1.

Characterization of the Recombinant Hemolysin

Hemolytic activity could not be detected in culture supernatants of *E. coli* DH5α expressing any of the hemolytic clones. This suggests that *E. coli* is unable to transport the recombinant hemolysin in a manner similar to that of the native organism. Employing an osmotic shock procedure, supernatant from *E. coli* DH5α(pJBA) was found to contain potent hemolytic activity. This activity was destroyed when supernatant was boiled or treated with pronase. In contrast, osmotic shock supernatants from *E. coli* DH5α (pSML5) or DH5α(pUC19) were totally non-hemolytic even when concentrated fourty-fold.

Unlike the hemolysins from *E. coli* which require calcium for activity (A. Ludwig, T. Jarchau, R. Benz, and W. Goebel. 1988. The repeat domain off *Escherichia coli* haemolysin (Hly A) is responsible for its $Ca^{2+}$-dependent binding to erythrocytes. Mol. Gen. Genet. 214:553–561.)the recombinant *T. hyodysenteriae* hemolysin is calcium independent. The addition of 50 mmol/l EDTA to osmotic shock supernatants of *E. coli* DH5α(pJBA) did not effect their ability to lyse SRBC.

Carbohydrates of varying molecular diameters have been utilized to determine the mechanism of hemolysin action (S. Bhakdi, N. Mackman, J. M. Nicaud, and I. B. Holland. 1986. *Escherichia coli* hemolysin may damage target cell membranes by generating transmembrane pores. Infect. Immun. 52:63–69. R. Scherrer and P. Gerhardt. 1971. Molecular sieving by the Bacillus megaterium cell wall and protoplast. J. Bact. 107:718–735.), thus, osmotic shock supernatants from *E. coli* DH5α (pJBA), DH5α(pSML5) and DH5α(pUC19) and the RNA-core hemolysin were added to SRBC that had been pre-treated with carbohydrates of increasing molecular diameter: sucrose (0.9 nm), raffinose (1.2 to 1.4 nm) and dextran 5000 (1.75 to 2.3 nm). These sugars would serve as osmoprotectants if the recombinant or native hemolysin was capable of lysing red blood cells by forming pores in the red blood cell membrane. All osmotic shock supernatants lysed carbohydrate pre-treated red blood cells.

The supernatant from DH5α(pJBA) revealed cytolytic activity as CHO cells incubated with 1:2 to 1:4 dilutions (16 and 8 HU, respectively) were killed within a 1 hour incubation period. Two-fold dilutions from 1:5 to 1: 160 of RNA core-hemolysin were as effective in killing CHO cells as was the recombinant hemolysin. Concentrated osmotic shock supernatants from DH5α(pSML) and DH5α(pUC19) had no cytolytic affect on the cells following a 24 hour incubation period nor did heated inactivated recombinant hemolysin.

CHO cells exposed to medium containing a 1:5 dilution of RNA-core buffer or heat-inactivated RNA coreohemolysin remained viable during the 24 hour incubation period with no observable CPE.

EXAMPLE 2

Cloned Hemolysin of *T. hyodysenteriae* Provide Partial Protection against Experimental Disease in Mice Materials and Methods Bacterial strains and growth conditions

*T. hyodysenteriae* C5, a Dutch field isolate that is pathogenic for OF-1 mice, was grown as described in EXAMPLE 1. Bacterial concentrations were determined with a hemocytometer under dark-field microscopy. *Escherichia coli* DH5αF'(Bethesda Research Laboratories Life Technologies, Inc., Gaithersburg, Md.) was used as recipient for plasmid transformations and was grown in LB media or on LB agar plates (Maniatis et al., 1982).

Mice

Female Ico: OF1 (OF-1) mice were obtained from lffa Credo (France) and housed in microisolator cages with free access to standard laboratory food and water.

Cloning and expression

Cloning and expression of the hemolysin (tly) gene of *T. hyodysenteriae* has been described in the foregoing example. Plasmid pJBA containing the tly gene was used in the polymerase chain reaction (PCR) to obtain a DNA fragment containing the entire reading frame of the gene of interest without adjacent non-coding sequences. Oligodeoxynucleotides (Pharmacia, Woerden, The Netherlands) 5'cgggatcccgATGCGATTAGATGAATATGT3' and 5'ggggaattccTCGTGATAATAATAGAAGCG3' (nucleotides 471 to 490 and nucleotides 1449 to 1430, respectively in SEQUENCE ID NO: 1 were used to amplify the hemolysin gene. Linker sequences, containing a BamHl or EcoRl restriction enzyme digestion site (designated in lowercase letters in the above oligodeoxynucleotide sequences), were added to facilitate cloning and expression of the amplified gene into plasmid pGEX-3X (Pharmacia) in frame with the glutathion-S-transferase (Gst) gene. Ten nanogram of template DNA were used in the PCR (35 cycles) with the following cycle parameters: 1 min at 95° C., 1 min at 48° C., 2 min at 72° C. PCR-amplified DNA segments were isolated by agarose gel electrophoresis, purified by GeneClean (Bio 101, La Jolla, Calif.), digested with EcoRl and BamHI and ligated in pGEX-3X. The recombinant plasmid pGEX-tly was used to transform *E. coil* DH5α. Expression of fusion protein will then be under control of the tac promoter, which is inducible with isopropyl-β-D-thiogalactopyranoside (IPTG).

Gst or recombinant hemolysin (GST-Hly) pas purified from induced cultures of *E. coil* containing respectively plasmid pGEX or PGEX/Tly by affinity chromatography as described by Fikrig et al. [E. Fikrig, S. W. Bartold, N. Marcanttonio, K. Deponte, F. S. Kantor, and R. A. Flavell. 1992. Roles of OspA, OspB, and flagellin in rpotective immunity to Lyme borreliosis in laboratory mice. Infect. Immun. 60: 657–661]and was used for immunization and in ELISA.

Vaccination and challenge of OF-1 mice

Mice were immunized and challenged by the schedule outlined in Table 4. Herein N is the number of mice per group; ip means intraperitoneal vaccination with Freund's incomplete adjuvant; o+ means oral vaccination, in the presence of 10 μg cholera toxin; o- means oral vaccination, without cholera toxin; For the challenge experiments the doses were administered intragastrically and contained $10^8$ logphase *T. hyodysenteriae* strain C5 (*T. hyo*) or culture medium (TSB)

TABLE 3

| Group | N | Antigen | Prime (day 0) | Boost (day 21) | Challenge (day 29 and 30) |
|---|---|---|---|---|---|
| 1 | 12 | — | — | — | *T. hyo* |
| 2 | 12 | — | — | — | TSB |
| 3 | 12 | Gst | ip | ip | *T. hyo* |
| 4 | 12 | Gst | ip | o+ | *T. hyo* |
| 5 | 12 | Gst/Hly | ip | ip | *T. hyo* |
| 6 | 12 | Gst/Hly | ip | o+ | *T. hyo* |
| 7 | 7 | water | ip | o+ | *T. hyo* |

Intraperitoneal (i.p.) immunization occured at the age of 5 weeks with 15 μg Gst or Gst-Hly in 0.3 ml of Freund's imcomplete adjuvant. Three weeks later mice received either an i.p. boost with the same amount of protein in Freund's incomplete adjuvant or an intragastric dose of 1.0 ml 0.2 mol/l Na₂HCO₃ containing 100 μg Gst or 100 μg Gst-Hly, with or without 10 μg cholera toxin (CT; C-3012, Sigma, St. Louis, Mo.). Seven days later mice were intragastrically challenged with $10^8$ *T. hyodysenteriae*. Mice were sacrificed by cervical dislocation 12 days later to evaluate signs of *T. hyodysenteriae* infection in the cecum: catarrhal inflammation, excess intraluminal mucus, oedema, hyperemia and atrophy. Cecal lesions were graded on a scale from 0 to 3:
grade 0 represents lack of lesions;
grade 1 indicates mild lesions;
grade 2 indicates moderate lesions and
grade 3 indicates severe lesions.
Serial dilutions of cecal contents were cultured and colony forming units (cfu) of *T. hyodysenteriae* per gram of cecal material were determined.

Collection of serum and preparation of gut homogenates

From five mice of each group serum was prepared from blood obtained by orbital puncture at day 0 and 21. These mice were sacrificed at day 29 by cervical dislocation and gut homogenates were prepared. The entire intestine was homogenized in an icecold solution of 5 ml 50 mmol/l EDTA containing 0.1 mg/ml soybean trypsin inhibitor (Sigma) and centrifuged at 6000×g for 10 min at 4° C. Two ml of supernatant were collected, to which 20 μl of 100 mmol/l phenylmethylsulphonyl fluoride (PMSF) (Sigma) in 95% ethanol were added and samples were centrifuged at 13,000×g for 30 min. To 1.5 ml of supernatant, 15 μl of 100 mmol/l PMSF and 15 μl of 1% sodium azide (Sigma) were added and the solution was left at room temperature for 10 min. Subsequently 100 μl of fetal calf serum were added and the samples were stored at −20° C.

Electrophoresis, Western blotting and ELISA.

Proteins were separated on 12.5% SDS-PAGE, transferred to nitrocellulose sheets, and detected with specific antibodies as described in Example 1. Antibodies against Gst and Gst-Hly were determined with ELISA. Ninetysix-well polystyrene microtiter plates (Greiner, Alphen a/d Rijn, The Netherlands) were coated overnight at 4° C. with 0.1 ml of a solution containing a previously determined optimal amount of soluble Gst, or Gst-Hly, obtained as described above, in carbonate buffer, pH 9.6. Wells were washed twice with PBS/0.1% Tween 20 (PBST). Fourfold dilutions of 1:20 diluted serum samples or undiluted gut washings were made in PBST and incubated in coated wells for 1 hour at 37° C. The wells were washed three times with tap water/0.01% Tween 20, and 1:1000 diluted peroxidase-conjugated goat-anti-mouse IgG or peroxidase-conjugated goat-anti-mouse IgA were added. The plates were further incubated for 1 hour at 37° C. The wells were washed three times with tap water containing 0.01% Tween. The substrate reaction was carried out by adding 100 μl of a freshly prepared solution containing 50 mg 2,2'-azino-bis(3'ethylbenzthiazolin 6-sulfonic acid and 25 μl 30% $H_2O_2$ in 100 ml 0.1 mol/l $Na_2HPO_4$-0.05 mol/l citric acid. After 30 min. incubation at room temperature the optical density at 405 nm was measured. Titers were defined as the maximum serum dilution that gave twice the $OD_{405}$ of non-immunized mice.

RESULTS

Production and purification of recombinant proteins

Figure 8A:
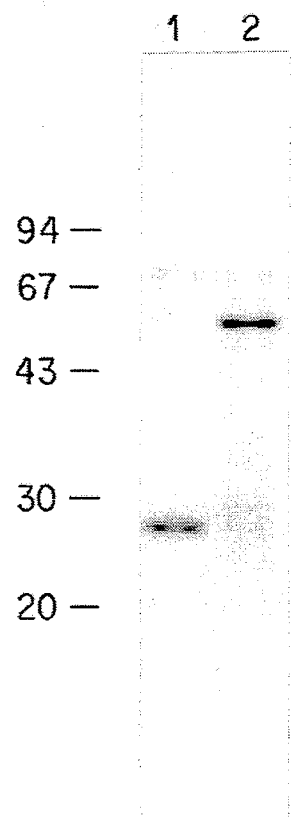
FIGS. 8A and 8B show that no contaminating proteins were detected in recombinant Gst and Gst-1Hy.
Figure 8B:
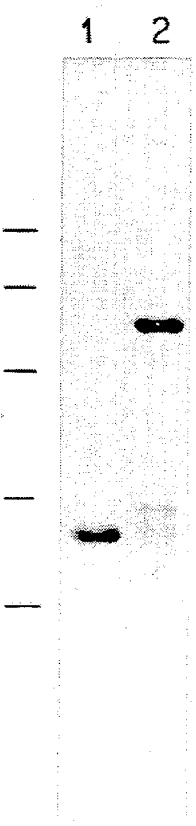

Recombinant Gst and Gst-Hly were purified from *E. coli* and analyzed by SDS-PAGE and immunoblotting to determine the purity of the preparations (FIG. 8 panels A and B, respectively). No contaminating proteins were detected: on immunoblots all protein bands in these preparations reacted with specific antisera against Gst (Panel B, lane 1 and 2, respectively).

Antibody response to *T. hyodysenteriae* recombinant proteins

We investigated the murine immune response to i.p. administration of Gst or Gst-Hly in Freund's incomplete adjuvant, followed by either an i.p. boost of antigen in Freund's incomplete adjuvant or an oral boost in the presence of cholera toxin. In Table 4 the groups are the same as defined in Table 3; the results are expressed as mean antibody titer per group of five mice. ND means not determined.

TABLE 4

| Group | serum IgG αGst | gut IgA αGst | serum IgG αGst-Hly | gut IgA αGst-Hly |
|---|---|---|---|---|
| 1 | 0 | 0 | 0 | 0 |
| 2 | 0 | 0 | 0 | 0 |
| 3 | 140,000 | 23 | ND | ND |
| 4 | 57,000 | 1 | ND | ND |
| 5 | ND | ND | 164,000 | 4 |
| 6 | ND | ND | 90,000 | 1 |
| 7 | 0 | 0 | 0 | 0 |

It can be concluded from Table 4 that i.p. immunization with Gst-Hly followed by an i.p. boost induced both detectable serum IgG antibodies and gut-IgA antibodies specific for Gst-Hly. When the i.p. prime was followed by an oral boost in the presence of cholera toxin, the serum IgG antibody response was significantly less, whereas specific IgA could not be detected. In non-immunized mice specific antibodies were not detected, neither in the serum, nor in the intestine.

Challenge with *T. hyodysenteriae*

To determine the role of hemolysin in protection, immunized mice and control mice were challenged orally with *T. hyodysenteriae* and evaluated for the presence of lesions in the cecum (Table 5). The group numbers in Table 5 correspond with those in Table 3. Each group consisted of seven mice. The results are expressed as group mean cecai score, plus or minus the standard deviation.

TABLE 5

| Group | cecal score |
|---|---|
| 1 | 2.4 ± 0.7 |
| 2 | 0 ± 0 |

TABLE 5-continued

| Group | cecal score |
| --- | --- |
| 3 | 2.0 ± 0.3 |
| 4 | 2.1 ± 0.6 |
| 5 | 1.5 ± 0.9 |
| 6 | 2.4 ± 0.4 |
| 7 | 2.2 ± 0.9 |

Non-immunized mice (group 1) or mice immunized with Gst (group 3 and 4) or water (group 7) had moderate to severe cecal lesions. Ceca were less affected in mice immunized twice i.p. with Gst-Hly (group 5). Mice immunized i.p with Gst-HLy and boosted orally with antigen in the presence of cholera toxin had cecal comparable to those observed in the control groups (group 6). Non-immunized mice inoculated with culture medium had no cecal lesions (group 2).

EXAMPLE 3
Immunization of Mice by Attenuated *Salmonella typhimurium* Expressing *T. hyodysenteriae* Antigens.
MATERIALS AND METHODS
Bacterial strains The vehicles used for the delivery of *T. hyodysenteriae* antigens to mice were *Salmonella* (*S.*) *typhimurium* SL3261, an aroA mutant kindly provided by B. A. D. Stocker, and *S. typhimurium* X3987, a Δcya Δcrp Δasd mutant. X3987 has a deletion of the chromosomal gene for β-aspartate semialdehyde dehydrogenase (Δasd) so that it is unable to grow in the absence of diaminopimelic acid (DAP), an essential constituent of the cell wall. *E. coli* DH5αF' (Bethesda Research Laboratories Life Technologies, Inc., Gaithersburg, Md.) was used as a transformation recipient of plasmid DNA. *E. coli* Δasd X6097 was used as an intermediate recipient of plasmid pYA292 and derivatives thereof.

Culture conditions

*S. typhimurium* and *E. coli* were grown in LB broth or on LB plates at 37° C. containing 50 µl g kanamycin/ml or 100 pg ampicillin/ml when appropriate [J. Sambrook, E. F. Fritsch, and T. Maniatis. 1989. Molecular cloning: a laboratory manual. Cold Spring Harbor Laboratory. Cold Spring Harbor, N.Y.]. Inocula for oral immunization with *S. typhimurium* were prepared by culturing strains in 500 ml LB (with the appropriate antibiotic) overnight at 37° C. with shaking (200 rpm). Cells were harvested by centrifugation (10,000×g, 10 min, 4° C.) and resuspended in 2 ml PBS, pH 7.2 to give a concentration of approximately $10^{10}$ colony forming units (cfu) per ml.

Plasmids

Plasmid pGEX-3X (Pharmacia) carries the gene for glutathion-S-transferase (Gst) under the control of the isopropyl-β-D-thiogalacto pyranoside (IPTG)-inducible tac promoter. Plasmid pUEX2 (Amersham, Buckinghamshire, UK) encodes β-galactosidase and is temperature controlled by the cro-cI857 gene. Plasmid pYA292 is an asd +cloning vector in which cloned antigens are under control of the Ptrc promoter Nakayama, K., S. M. Kelly, and R. Curtiss III. 1988. Construction of an Asd+ expression-cloning vector: stable maintenance and high level expression of cloned genes in a Salmonella vaccine strain. Bio/Tech. 6:693–697]. The vector complements the chromosomal Δasd deletion of X3987 and thus is stably maintained in X3987 when grown in the absence of DAP, e.g. in mammals, were DAP is not present. Plasmid pLUC108.2 contains the multiple cloning site and the first bases of LacZa gene from pUC8.2 [Z. Hanna, C. Fregau, G. Préfontaine, and R. Brousseau. 1984. Construction of a family of universal expression plasmid vectors. Gene 30:247–250.], cloned into plasmid pLG338, which is a derivative of plasmid pSC105 [Stoker, N. G., N. F. Fairweather, and B. G. Spratt. 1982. Versatile low-copy-number plasmid vectors for cloning in *Escherichia coli*. Gene 18:335–341.]. The plasmid is present at 6 to 8 copies per cell. Expression is from the lac promoter.

Construction of vectors containing a *T. hyodysenteriae* sheath flagellar gene

The hemolysin gene tly of *T. hyodysenterae* were cloned and their nucleotide sequence determined as described. Chromosomal DNA was isolated as described in Example 1. Ten nanograms of plasmid pJBA containing the tly gene was used in the polymerase chain reaction (PCR) to obtained a DNA fragment containing the entire reading frame of the gene of interest. Oligonucleotides (Pharmacia, Woerden. The Netherlands) used for amplification were based on the known nucleotide sequence of tly and were flanked by a linker sequence containing a BamHI or EcoRI restriction enzyme degestion site to facilitate cloning and expression. Primers 5'cgggatcccgAT-GCGATTAGAT-GAATATGT3'and 5'gggaattccTCGT-GATAATAATAGAAGCG3'(nucleotides 471 to 490 and nucleotides 1449 to 1430, respectively in SEQUENCE ID NO: 1 were used to amplify a fragment containing the tly gene sequence. Cycle parameters were: 1 min at 95° C., 1 min at 35° C. and 2 min at 72° C. PCR-amplified DNA fragments were purified by GeneClean, digested with EcoRI and BamHI and ligated into plasmid pYA292, pLUC108.2, pGEX-3X and pUEX2. In pYA292 a non-fusion protein is encoded. With pLUC108.2 a fusion to the lacZa peptide (1.2 kD) is made, whereas with pGEX-3X a fusion protein to Gst (27.5 kD) is made and with pUEX2 a fusion with β-galactosidase (116 kD).

*E. coli* and *S. typhimurium* genetic manipulations

Recombinant plasmids containing tly were used to transform *E. coli* by electroporation [W. J. Dower, J. F. Miller, and W. Ragsdale. 1988. High efficiency transformation of *E. coli* by high voltage electroporation. Nucleic Acids Res. 13:6127–6144.]Plasmids encloding production of recombinant hemolysin (Tly) were purified from *E. coli* by cesium chloride gradient centrifugation and used to transform *S. typhimurium* by electropotation. Transformants were screened for antibiotic resistance (pLUC108.2, pGEX-3X, pUEX2) or growth in the absence of DAP (pYA292). Transformants were tested for recombinant Tly production by immunoblot analysis of 50 µl of a 40 ml overnight culture washed once in phosphate buffered saline, pH 7.0 (PBS). To verify that electroporation of S. typhimurium had not selected for rough routants, the LPS profile of transformants was examined by using SDS-PAGE and silver staining [P. J. Hitchcock, and T. M. Brown. 1983. Morphological heterogeneity among Salmonella lipopolysaccharide chemotypes in silver-stained polyacrylamide gels. J. Bacteriol. 154:269–277.]

In vitro stability of plasmids

Overnight cultures of S. typhimurium transformant in LB broth were diluted 100-fold in fresh medium and incubated for an additional 8 hours. Subsequently, these cultures were diluted again 100-fold in fresh medium and incubated overnight. Serial dilutions of each subculture were plated on LB plates with and without the appropriate antibiotic.

Immunization of mice, enumeration of bacteria in mouse organs, collection of sera and gut washings BALB/c females of 10 weeks of age were orally dosed using a gavage needle with $10^{10}$ cfu of the S. typhimurium vaccine strain at day 0 and day 21. At 7, 14 and 21 days after the first dose, groups of 3 animals were sacrifled and the number of Salmonellae present in the livers and spleens was determined. Livers and spleens were homogenized in sterile distilled water using a stomacher. Viable counts were performed on these homogenates in duplicate on LB plates supplemented with and without antibiotic to determine the retention of the recombinant plasmids in the colonies recovered from mice immunized with strains containing pLUC108.2, pGEX-3X or pUEX2 plasmid. Expression of Tly in these recombinant S. typhimurium was examined. Nitrocellulose filters (Hybond C. Amersham) were laid over LB plates and recovered cells were streaked onto the nitrocellulose. After overnight incubation at 37° C. the filters were lifted, exposed to chloroform vapour for 1 hour and washed 4 times in PBS containing 0.05% Tween. Immunoscreening of the filterlifts was performed with specific antisera against Tly similar as with immunoblots (see below). In mice sacrificed at day 42 serum and gut antibody response to S. typhimurium and T. hyodysenteriae antigens was determined with ELISA. Blood samples were collected by tail bleeds, or cardiac puncture from mice anaesthesized with halothane, 3 weeks after the first and second oral doses. Blood was mixed with an equal volume of a solution of 85 mmol/l tri-sodium citrate-65 mmol/l citric acid, centrifuged at 6000×g and supernatant was stored at −20° C. Gut samples were prepared from minced small intestine as described in Example 2.

SDS-PAGE, immunoblotting (Western blotting) and ELISA

Proteins were separated on 12.5% SDS-polyacylamide gels (SDS-PAGE) and visualized by Coomassie Brilliant Blue R 250 staining. After electrophoretic transfer to nitrocellulose filters, proteins were reacted with specific antiserum and bound antibodies were visualized with alkaline phosphatase conjugated antibodies as described. Antibodies specific for recombinant Tly were detected in ELISA as described in Example 2.

Titers were measured as the $OD_{405}$ of 1/750 dilutions of sera or 1/16 dilutions of gut homogenates, minus the avarage values obtained with four non-immunized mice.

Immunological reagents

Polyclonal antiserum against Tly was prepared by immunizing rabbits with denatured Tly isolated from Western blots Gst and Gst-Tly were obtained by affinity chromatography from E. coil expressing these antigens according to Example 2. One hundred μg purified Gst was emulsified in Freund's complete adjuvant in a final volume of 3 ml and injected subcutaneously and intramuscularly into New Zealand White rabbits on day 0 and day 21. Serum collected at day 34 was used in immunoblotting experiments and in ELISA.

RESULTS

Figure 9:
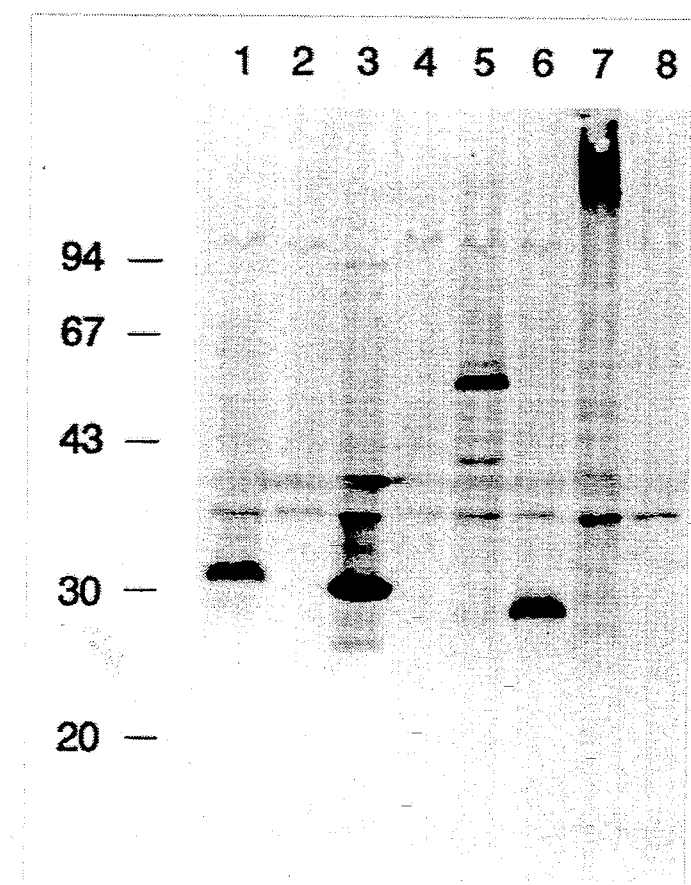
FIG. 9 is an immunoblot showing expressed Tly in transformants directing the synthesis of *T. hyodysenteriae* Tly.

In vitro expression of recombinant T. hyodysenteriae proteins by attenuated S. typhimurium Plasmids directing the synthesis of T. hyodysenteriae Tly were transformed to S. typhirnurium SL3261 (plasmids pLUC108.2, pGEX-3X, pUEX2) or S. typhimurium X3987 (plasmid pYA292) by electroporation. All transformants tested were smooth as judged by LPS specific staining of proteinase K treated whole cell lysates (not shown) and expressed recombinant Tly as shown by immunobiotting (FIG. 9).

Because SL3261 and X3987 do not carry the lacI gene on the chromosome protein expression with pGEX3X, pLUC108.2 and pYA292 plasmids is constitutive. Heterologous antigen expression by bacteria containing pUEX2 plasmid was constitutive as well, since these bacteria were grown at the permissive temperature. Molecular mass of recombinant Tly (fusion) protein encoded by pLUC108.2, pYA292, PGEX-3X and pUEX2 is 30, 27, 58 and 146 kDa respectively (FIG. 9). Important differences in level of expression were observed. S. typhirnurium containing tly constructs produced significant amounts of recombinant Tly, with expression by X3987(pYA292/tly) being highest. Plasmid pYA292 is stably maintained in T. hyodysenteriae X3987. In order to determine the in vitro stability of the other plasmids, vaccine strains were passaged repeatedly in medium without antibiotic. When serial dilutions of the subcultures were plated on LB plates with and without appropriate antibiotic, the presence of antibiotic had no significant effect on the number of cfu obtained with S. typhirnurium SL3261 containing pGEX-3X, pLUC108.2 or derivatives, thus demonstrating reasonable stability of these plasmids in the host bacteria under these conditions.

Colonization of liver and spleen of mice orally infected with Salmonella vaccine strains BALB/c mice were dosed orally with $10^{10}$ cfu of S. typhimurium vaccine strain producing recombinant Tly protein. At day 7, 14 and 21 after infection livers and spleens were examined for the presence of vaccine strain (Table 6). The results in this table are expressed as colony forming units (cfu) per organ, and were determined in the presence or absence of the appropriate antibiotic; ND means not determined.

Vaccine strains containing pGEX, pYA292 or pLUC without insert were only monitored at day 7. Results obtained with livers are shown in Table 7 and are similar as those obtained with spleens. At day 7×X3987 (pYA292) and X3987 (pYA292/tly) were found in livers in high numbers (respectively $3.7 \times 10^3$ or more, and $4.5 \times 10^3$ or more bacteria per organ). Similar numbers of SL3261 containing pLUC were detected in livers of two mice; in the third mouse no salmonellae were detected. With *S. typhimurium* containing pGEX 10 to 600 bacteria per liver were isolated. In only one animal could SL3261 (pLUC/tly) be detected in low numbers. No salmonellae carrying pGEX/tly were ever reisolated from livers or spleens. Fourteen days post dosing only X3987(pYA292/tly) and SL3261(pLUC/tly) were found in livers and spleens; by 21 days only X3987(pYA2921tly) was reisolated. All salmonellae isolated from livers and spleens expressed the cloned antigen. All salmonellae isolated at day 7 from this animal had lost the plasmid, whereas at day 14 almost half of the recovered salmonellae did not contain the plasmid.

TABLE 6

| vaccine | mouse | no. of cfu day 7 | day 14 | day 21 | no. of antibiotic resistant cfu day 7 | day 14 | day 21 |
|---|---|---|---|---|---|---|---|
| pYA292 | 1 | 4500 | ND | ND | ND | ND | ND |
|  | 2 | 6300 | ND | ND | ND | ND | ND |
|  | 3 | 3700 | ND | ND | ND | ND | ND |
| pYA292/ tly | 1 | 8000 | 500 | 530 | ND | ND | ND |
|  | 2 | 4500 | 200 | 515 | ND | ND | ND |
|  | 3 | 16000 | 650 | 150 | ND | ND | ND |
| pLUC | 1 | 5800 | ND | ND | 4900 | ND | ND |
|  | 2 | 1800 | ND | ND | 1400 | ND | ND |
|  | 3 | 0 | ND | ND | 20 | ND | ND |
| pLUC/ tly | 1 | 50 | 320 | 0 | 50 | 400 | 0 |
|  | 2 | 0 | 50 | 0 | 0 | 60 | 0 |
|  | 3 | 0 | 0 | 0 | 0 | 0 | 0 |
| pGEX | 1 | 600 | ND | ND | 700 | ND | ND |
|  | 2 | 40 | ND | ND | 10 | ND | ND |
|  | 3 | 10 | ND | ND | 10 | ND | ND |
| pGEX/ tly | 1 | 0 | 0 | 0 | 0 | 0 | 0 |
|  | 2 | 0 | 0 | 0 | 0 | 0 | 0 |
|  | 3 | 0 | 0 | 0 | 0 | 0 | 0 |

Murine antibody response to *S. typhimurium* and *T. hyodysenteriae* antigens Serum and gut homogenates from mice killed 3 weeks after they had received an oral boost of $10^{10}$ salmonellae vaccine strain were analyzed by ELISA for antibodies against whole salmonellae sonicate, recombinant Tly. All mice had developed an immunoglobulin anti-salmonella titer in gut homogenates, though the degree of response varied between vaccine constructs (Table 7). All three pLUC constructs induced potent gut antibody responses to salmonella sonicates. The responses to the pGEX vaccines were different again, 3 of the 4 mice responded poorly to the Sl3261 (pGEX) vaccines, yet 4 of 4 mice responded well to SL3261 (pGEX/t/y). As seen in the gut, the serum antibody responses to salmonellae sonicates varied between vaccine constructs, and were not directly related to the relative magnitude of the responses seen in the gut (Table 7). Highest serum responses were found in mice immunized with X39879(pYA292), X3987/pYA292/tyl) or SL3261(pLUC), whereas oral immunization of mice with SL3261 containing pGEX derivatives resulted in a serum anti-salmonella response just above those measured in non-immunized animals.

TABLE 7

| mouse | pYA292 | pYA292/ Tly | pLUC | pLUC/ Tly | pGEX | pGEX/ Tly |
|---|---|---|---|---|---|---|
| gut IgA antibody | | | | | | |
| 1) | 1.407 | 0.201 | 1.439 | 0.279 | 1.180 | 1.513 |
| 2) | 0.808 | 1.237 | 1.570 | 1.360 | 0.298 | 1.604 |
| 3) | >3 | 1.396 | 1.299 | 0.948 | 0.146 | 1.406 |
| 4) | >2 | >2 | 0.831 | 0.734 | 0.900 | 1.493 |
| serum IgG antibody | | | | | | |
| 1) | 0.725 | 0.069 | 0.564 | 0.599 | 0.235 | 0.290 |
| 2) | 0.759 | >2 | >2 | 0.740 | 0.246 | 0.222 |
| 3) | >2 | 0 | >2 | 0 | 0.304 | 0.342 |
| 4) | >2 | >2 | 0.371 | 0 | 0.147 | >2 |

The results in this table are given at $OD_{405}$ of 1:16 diluted gut washings or 1:750 diluted serum samples for each of four mice of each group aninals, minus the average value obtained with four non-immunized animals (0.207, and 0.284 respectively).

---

We claim:

1. An isolated polynucelotide selected from the group consisting of:
   a. DNA having the nucleotide sequence represented in SEQUENCE ID No. 1 or a fragment thereof wherein said DNA codes for a peptide able to elicit an immune response against *Treponema hydoysenteriae*;
   b. polynucleotides which hybridize under stringent conditions to the DNA set forth in SEQUENCE ID No. 1 and which code for a polypeptide having antigenic properties of the hemolysin protein of *Treponema hyodysenteriae*; and
   c. "degenerate DNA molecules which code for the amino acid sequence set forth in SEQUENCE ID. No. 2".

2. An expression vector comprising a polynucleotide according to claim 1 wherein said vector is capable of directing the expression of said polynucleotide when said vector is present in a suitable host cell.

* * * * *